United States Patent [19]

Bower

[11] 4,276,175

[45] Jun. 30, 1981

[54] REGENERATABLE PERITONEAL DIALYSIS BAG

[76] Inventor: John D. Bower, 140 Chippewa Cir., Jackson, Miss. 39211

[21] Appl. No.: 58,931

[22] Filed: Jul. 19, 1979

[51] Int. Cl.³ .................. B01D 13/00; A61M 1/03
[52] U.S. Cl. ........................ 210/636; 128/213 A; 210/641; 210/646; 210/648
[58] Field of Search ........... 210/22, DIG. 23, 321 B, 210/321 A, 321 R; 128/272, 213 A, 214 R

[56] References Cited

U.S. PATENT DOCUMENTS

| | | | |
|---|---|---|---|
| 3,518,982 | 7/1970 | Timmins et al. | 128/2 |
| 3,608,729 | 9/1971 | Haselden | 210/321 B |
| 3,616,930 | 11/1971 | Muir | 210/321 B |
| 3,640,393 | 2/1972 | Hurtig | 210/321 R |
| 3,774,762 | 11/1973 | Lichtenstein | 210/321 B X |
| 3,799,873 | 3/1974 | Brown | 210/22 |
| 3,825,493 | 10/1974 | Brown et al. | 210/321 R |
| 3,864,259 | 2/1975 | Newhart | 210/88 |
| 3,884,808 | 5/1975 | Scott | 210/321 B |
| 3,962,094 | 6/1976 | Davis et al. | 210/321 R |
| 4,025,436 | 5/1977 | Tsupa et al. | 210/321 A |
| 4,081,372 | 3/1978 | Atkin et al. | 210/321 A X |
| 4,173,537 | 11/1979 | Newhart | 210/323 R X |

FOREIGN PATENT DOCUMENTS 40-4816  3/1965  Japan ............................ 210/22

OTHER PUBLICATIONS

Oreopoulos et al., "A Simple and Safe Technique for Continuous Ambulatory Peritoneal Dialysis", (CAPD), TASAIO, 1978, pp. 484-489.

Moncrief et al., "Additional Experience with Continuous Ambulatory Peritoneal Dialysis",(CAPD), TASAIO, 1978, pp. 476-483.

*Primary Examiner*—Frank A. Spear, Jr.
*Attorney, Agent, or Firm*—Geoffrey L. Chase; Martin P. Hoffman

[57] ABSTRACT

A regeneratable peritoneal dialysis bag having a hollow fiber filtration bundle affixed to flexible plastic sidewalls so as to regenerate peritoneal fluid within the bag. An orifice in the bag allows for fluid connection with a peritoneal cavity. A method for use of such bag to regenerate peritoneal dialysate is also disclosed.

7 Claims, 3 Drawing Figures

REGENERATABLE PERITONEAL DIALYSIS BAG

BACKGROUND OF THE INVENTION

Peritoneal dialysis is a recognized treatment for end-stage renal failure in which dialysis fluid is introduced from a sterile source into the peritoneal cavity of a patient suffering end-stage renal failure. The dialysis fluid exchanges metabolites from the patients blood through the peritoneal membrane. The dialysis fluid containing metabolites is then removed from the peritoneal cavity.

Peritoneal dialysis is distinguishable from hemodialysis in which direct cleansing of the patient's blood is performed outside of the body by means of synthetic membranes in an artificial kidney machine having fluid connection with the patient's blood stream. Hemodialysis has three major disadvantages: the need (a) for large quantities of dialysis fluid, (b) the requirement that the dialysis fluid be isotonic to the blood so as to prevent electrolyte content of the blood from being diminished, and (c) the limitation to intermittent operation of the blood cleansing cycle due to the necessity of fluid connection of the patient to an artificial kidney machine for long periods of time. Such intermittent operation results in the maintenance of periodically high and then low concentrations of the toxic metabolites in a patient's blood, with corresponding adverse side effects.

With the use of peritoneal dialysis, cleansing or metabolite exchange of the blood with dialysis fluid occurs for the full period of time that dialysis fluid resides in the peritoneal cavity. Such exchange time is limited only by the requirement to drain the dialysis fluid from the peritoneal cavity, when such fluid has reached equilibrium with the blood, and to provide fresh fluid to the peritoneal cavity. Therefore, such dialysis systems have come to be termed continuous peritoneal dialysis as distinguished from intermittent dialysis, such as hemodialysis.

Continuous peritoneal dialysis is performed either on a truly continuous basis, as described in U.S. Pat. No. 3,825,493 to Brown et al., by circulating dialysis fluid through the peritoneal cavity and subsequently a filtration and makeup apparatus, or by periodic removal of infused dialysis fluid from the peritoneal cavity and replacement with fresh dialysis fluid, as described by D. G. Oreopoulos et al., Vol. XXIV Trans. Am. Soc. Artif. intern. Organs 1978. The latter system is only limited by the time required to drain the peritoneal cavity and to provide fresh dialysis fluid to said cavity.

The dialysis system described by Brown et al. suffers from the disadvantages of requiring two catheter connections to the peritoneal cavity for circuitous fluid flow, the bulk and expense of providing a complete ambulatory filtration and makeup apparatus to be worn by the patient and the requirement of high speed pumping of the peritoneal fluid.

In U.S. Pat. No. 3,799,873 to Brown, a peritoneal dialysis apparatus is described with a circuitous fluid flow path between the peritoneal cavity and a dialysing apparatus similar to Brown et al., above. Brown requires the circulation of the peritoneal fluid continuously with a complex, bulky and expensive exchange, filtration and makeup apparatus or a double fluid circuit system. The disadvantages of such an apparatus, designed for ambulatory use, but requiring several fluid reservoirs, a power source and a pumping means, are obvious.

D. G. Oreopoulos, M. Robson, S. Izatt, S. Clayton, and G. A. deVeber; *A simple and Safe Technique for Continuous Ambulatory Peritoneal Dialysis (CAPD)*, Vol. XXIV Transactions of American Society of Artifical Internal Organs (1978) p. 484 and J. W. Moncrief, K. D. Ralph, J. Rubin and R. P. Popovich; *Additional Experience with Continuous Ambulatory Peritoneal Dialysis (CAPD)*, Vol. XXIV Transactions of American Society of Aftificial Internal Organs (1978) p. 476 describe a peritoneal dialysis system which utilizes individual bags of fresh dialysis fluid which are infused into the peritoneal cavity of a patient by means of a simple flow line. The fluid is allowed to equilibrate with the blood across the peritoneal membrane, and, when equilibrium is achieved, the fluid is returned to the bag. The bag is then disconnected from the patient's peritoneal catheter. A fresh bag of dialysis fluid is needed for the next infusion. Five infusions per day for six days a week are prescribed. This system suffers from the disadvantages of the large amount of fresh dialysis fluid required, the need for numerous sterile dialysis bags, and, most important, the requirement for frequent sterile connections and disconnections of the dialysis bag to the peritoneal catheter. The latter requirement creates opportunities for infection and the development of peritonitis. Peritonitis can preclude the use of peritoneal dialysis during the duration of such an infection, or, at the minimum, require additional treatment of the patient with antibiotics.

All of the systems described above have the additional disadvantage of protein loss in the dialysis process. The peritoneal fluid infused in the body absorbs proteins from the body. This protein is lost from the body when the fluid is removed permanently from the body or when the protein containing fluid is filtered and recirculated. Proteins do not normally pass through the filtration or exchange membranes of fine structure such as used in such dialysis systems.

Other prior art references concerned with dialysis, but not highly relevant to this subject include U.S. Pat. Nos. 3,518,982; 3,864,259, 3,884,808 and 3,962,094.

SUMMARY OF THE INVENTION

With a recognition of the problems of the prior art dialysis systems, the present invention provides an apparatus and method which overcome the disadvantages identified with the prior art.

Specifically, the present invention is directed to a regeneratable peritoneal dialysis system which; (a) drastically reduces the number of dialysis bags required for maintenance of a patient, (b) diminishes the volume of peritoneal fluid needed for successful long term dialysis, and (c) reduces the repetition of sterile connections and disconnections to the peritoneal catheter necessary for dialysis, with its attendant potential for development of peritonitis infections.

In addition, the present invention overcomes the problem of protein loss by re-infusing the same dialysis fluid that was previously drained from the peritoneal cavity and by precluding the need for direct filtration of the drained peritoneal fluid. By preventing protein loss, dietary protein supplementation, which is required with other dialysis methods, is obviated.

These and other objectives of the invention are achieved by performing continuous ambulatory peritoneal dialysis utilizing a dialysis bag which has a hollow fiber filtration bundle affixed within the bag itself. This provides a means for regenerating the drained dialysis fluid without loss of protein from said fluid and without the requirement for sterile connections or disconnections after initial infusion.

The dialysis procedure of this invention involves the infusing of a fresh bag of dialysate into the peritoneal cavity, the equilibration of said dialysate with the patient's blood across the peritoneal membrane and then the removal of the dialysate from the peritoneal cavity to the dialysis bag. The dialysate, which contains metabolic waste products from the bloodstream, is then regenerated inside the dialysis bag, without the need to disconnect the bag from the patient. Regeneration is performed by equilibrating the metabolite containing dialysate with circulated make-up dialysate across the hollow fiber membranes affixed in the interior of the dialysis bag. The cleansed dialysate is then reintroduced into the peritoneal cavity for further exchanges with the blood of the patient. The regeneration step requires that the headers of the filtration means be connected to an artifical kidney machine or other circulatory means for supplying make-up dialysate, but these connections do not require sterile conditions because bacteria cannot cross the hollow fiber membrane to the peritoneal dialysate.

These and further objects and advantages of the present invention will become apparent from the discussion of a preferred embodiment of said invention as follows herewith.

BRIEF DESCRIPTION OF THE DRAWINGS

The invention will be further described as to the illustrative embodiments thereof in connection with the attached drawings wherein.

DESCRIPTION OF THE PREFERRED EMBODIMENT

Figure 1:
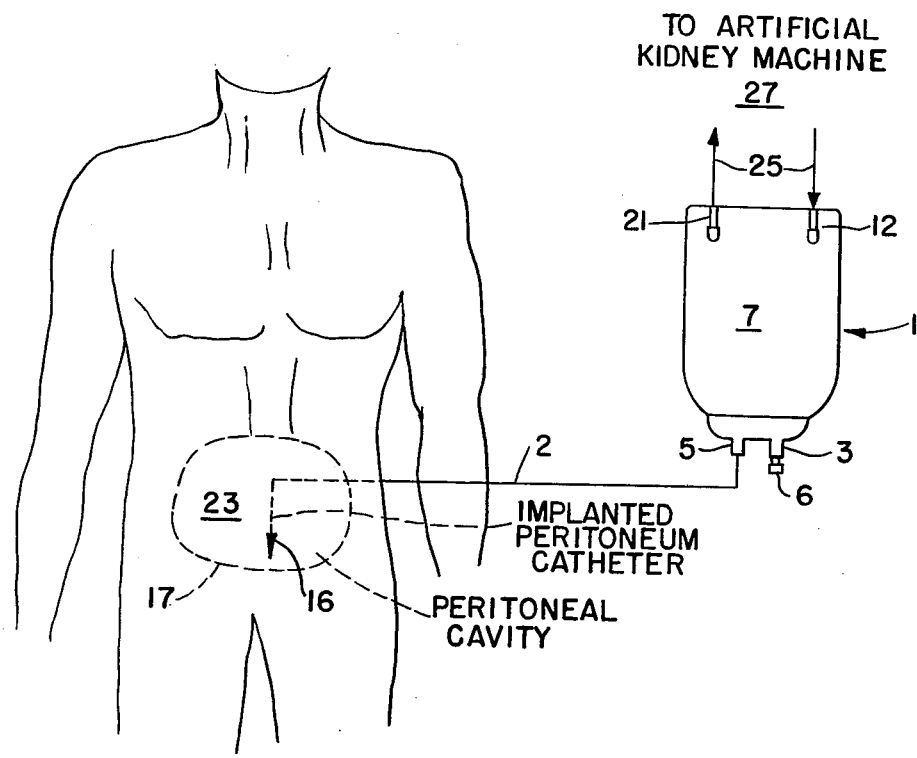
FIG. 1 is a schematic representation of the dialysis bag connected for infusion.

Referring to FIG. 1, the regenerative peritoneal dialysis bag 1 is shown. The bag can be constructed of any impervious flexible material such as an inert plastic of polyvinyl chloride (Travenol Dianeal 2000 ml #3B5346). The bag is sealed about its edge by heat sealing or other means to provide a leak-proof sterile sealed edge 9. The bag has at least one, and preferably two, orifices 3, 5 at one edge of the bag. A peritoneal fluid communicating orifice 5 is connected to a fluid flow line 2 which ends with a catheter 16 located in the peritoneal membrane 17 of the peritoneal cavity 23. Approximately 2 liters of dialysate is delivered from the dialysis bag 1 to the peritoneal cavity 23 for equilibration through the peritoneal fluid orifice 5. Additional components, such as antibiotics, can be added to the dialysate from time to time as needed by means of the auxiliary orifice 3. Each orifice is capped by a sterile sealing cap 4, 6. Regeneration of the peritoneal dialysate is performed by a filtration means 11 affixed in the bag 1.

Figure 2:
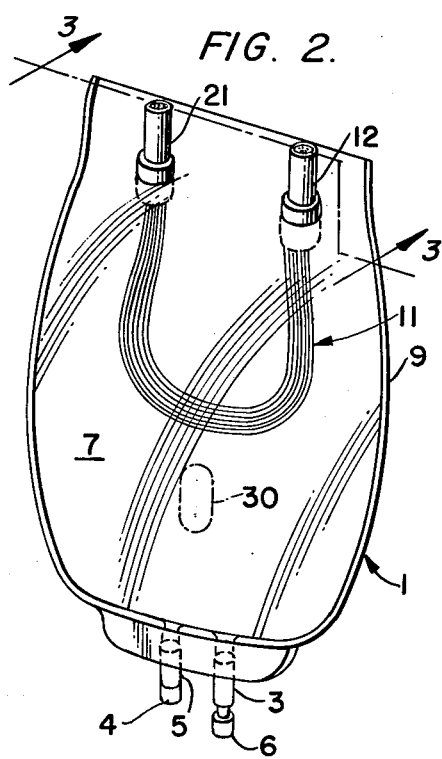
FIG. 2 is a schematic view of the dialysis bag of the present invention.

As shown in FIG. 2, the dialysis bag 1 comprises edge sealed sidewalls 7, one of which sidewalls includes apertures for the location of two headers 12, 21 of identical construction. The headers 12, 21 contain the ends of the hollow fiber bundle 13 which makes up the filtration means 11. The headers are sealed to the sidewall 7 to provide a sterile fluid impervious mounting for the filtration means 11.

This bag structure provides a sterile, fluid-tight enclosure for the peritoneal dialysate, while at the same time providing access to such dialysate for a make-up dialysate circulated through the hollow fiber bundle 13. The bundle comprises an array of generally axially parallel hollow fibers 15, each of which carries make-up dialysate, which absorbs metabolites across the fiber membrane from the peritoneal dialysate until equilibrium is reached. The hollow fibers are approximately 35 cm long and are selected so as to allow passage of metabolic by-products from the peritoneal dialysate to the make-up dialysate without removal of the larger protein components contained in the peritoneal dialysate. In addition, said fibers preclude the passage of bacteria from the make-up dialysate to the bag interior. It has been found that a bundle of 300 cellulosic hollow fibers, such as Enka-Glanzstoff types C11M and D21M, are sufficient for the necessary parameters of the filtration means. However, the dimension of the 2 liter dialysis bag is sufficient to allow considerably more fibers of longer length than set forth above. Regeneration times can be desirably shortened by such increases in magnitude of the fibers.

Figure 3:
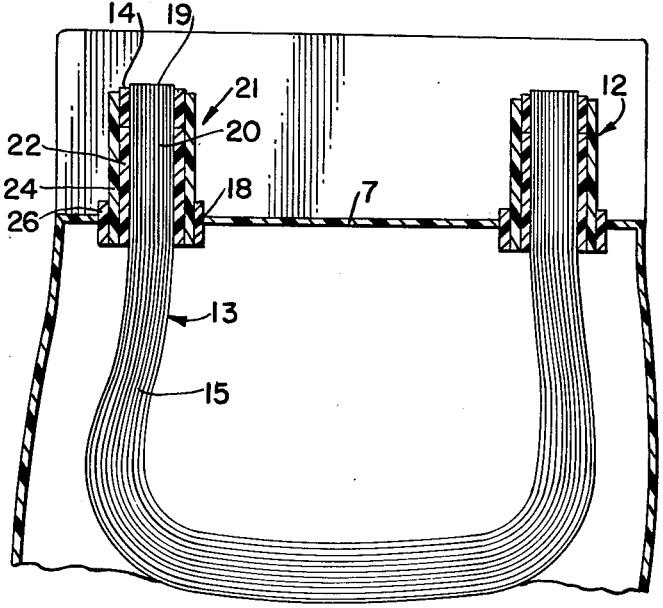
FIG. 3 is a partial sectional view taken through line 3—3 of FIG. 2 and in the direction indicated.

As indicated in FIG. 3, the hollow fiber bundle 13 is mounted at both of its ends 19 in a header 12, 21 by means of a polyurethane potting resin 20 cured around and in between the fibers 15. The fibers are contained within the header interior wall 22 which in turn is sealed to the header exterior wall 24 to provide a rigid durable support point. This header assembly is mounted in a flange 26 which constitutes the header-bag interface. The flange is solvent and heat sealed to the bag sidewall 7 in a sterile, fluid tight bond. The immediate ends of the fibers are encircled by a seal plug 14 so that potting resin does not contact and occlude the open bores of the fibers' ends. The header assembly can be fabricated from polyvinyl chloride.

The dialysis bag 1 performs satisfactory exchanges of metabolic by-products in a static condition, but the rate of equilibration of such metabolites across the fiber membrane is directly related to the effective contact surface provided to the entire volume of peritoneal dialysate. Therefore, the equilibrium is obtained more rapidly by agitation of the peritoneal dialysate in the bag. This can be achieved by placing the bag on a vibratory support during regeneration, or, alternatively by fabricating the bag with a magnetic stirrer 30 inside said bag with spinning of said stirrer by an exterior magnetic stirring motor during regeneration. Such agitating devices are conventional in the art and are not disclosed here.

After infusion of the dialysate from the bag into the peritoneal cavity and return of the dialysate to the bag, the headers 12, 21 are connected to an artificial kidney machine 27 or other fresh dialysate circulation means. The peritoneal dialysate is regenerated by resetting determined glucose values, resetting electrolyte levels and adjusting the fluid volume by controlled ultrafiltration in the fibers. During regeneration, there is no need to maintain precise sterile conditions at the filtration means. Sterile conditions are maintained at the peritoneal fluid orifice 5 because the catheter 16 and flow line 2 are not disconnected from the patient during the procedure.

During regeneration, ultrafiltration of some of the increasing fluid volume of the bag is necessary to offset the osmotic pressure effects of protein diffusing into the peritoneal fluid. Such protein has a similar effect to glucose of pulling additional water across the peritoneal membrane due to increased osmotic pressure. The resulting increased fluid volume is reset by operating the hollow fiber filtration means in an ultrafiltration manner rather than in an equilibrating manner. Such ultrafiltration can be performed by applying negative pressure across the hollow fiber membrane by means of the artificial kidney machine 27.

A patient suffering from end-stage renal failure uses the dialysis bag in the following procedure. A fresh 2 liter supply of dialysate is porvided in the sterile dialysis bag. The peritoneal fluid orifice of the bag is connected by sterile technique to the catheter and flow line of the patient and the dialysate is infused by gravity into the peritoneal cavity. The flow line is clamped shut by conventional means and the empty bag is rolled up and placed in a belt against the patient's abdomen. The infused dialysate is allowed to equilibrate with the patient's blood for a sufficient time, which may vary, but which approximates intervals sufficient for 5 exchanges per day. The flow line is then unclamped and toxic metabolite containing dialysate is gravity drained into the unrolled bag.

While still connected to the patient, the dialysis bag is connected by its headers to appropriate connections of an artificial kidney machine or other circulatory means, and the peritoneal dialysate is regenerated with fresh make-up dialysate. The headers are then disconnected, capped and the regenerated dialysate is re-infused into the peritoneal cavity. Five exchanges per day are performed for six days a week. No limitation on the number of such exchanges exists short of the limits of the mechanical integrity of the bag and filtration unit.

As stated previously, regeneration can be assisted by agitation or stirring to provide diminished regeneration times and less per-patient use of an artificial kidney machine. The absence of repeated connections and disconnections significantly reduces the incidence of peritonitis. Finally, protein loss is avoided because of the re-infusing of the same dialysis fluid.

Beyond the clinical improvements, the practical utility of regenerative peritoneal dialysis is enhanced by the significant cost savings of the dialysis system of this invention over other dialysis systems. Present prices for dialysis bags of fresh dialysate are six dollars for 2 liter bags. At the recommended five exchanges per day for six days, a cost of $180.00 per week is accrued. Similar expenses can be calculated on a yearly basis. This invention allows for the continued reuse of both bag and dialysate, so as to significantly eliminate such costs and bring peritoneal dialysis to a more readily affordable level.

The invention as set forth above is exemplified in a preferred embodiment, but those skilled in the art will contemplate departures from the details of the invention without departing from the scope of the invention as claimed below such as the inclusion of the headers in the edge seams of the bag wherein they can communicate through the exterior in a similar manner as in the preferred embodiment.

I claim:
1. A regeneratable ambulatory peritoneal dialysis bag comprising;
   a. two flexible sidewalls having leak-proof sterile sealed edges,
   b. a single sealable peritoneal fluid communicating orifice in said bag,
   c. two headers communicating through the exterior of said bag, said headers mounted in a flange which is solvent and heat sealed to the bag sidewall,
   d. a filtration means constructed and arranged for intermittent circulation of make-up dialysate through said bag consisting of a hollow fiber bundle mounted in said bag with the fiber ends encircled with a seal plug and sealed with a cured potting resin in said headers, said fibers selected so as to allow passage of metabolic by-products across the fiber wall without removal of proteins from the peritoneal dialysate.

2. The invention of claim 1 in which the bag has two orifices comprising a peritoneal fluid orifice and an auxiliary fluid communicating orifice for providing independant access to introducing additional components to the dialysate in said bag.

3. The invention of claim 1 wherein the bag is constructed of flexible polyvinyl chloride.

4. The invention of claim 1 wherein the bag includes a magnetic stirrer located in the interior of the bag for free movement.

5. A method for continuous removal of toxic metabolites from the blood by peritoneal dialysis, in which a single connection is made from a patient's peritoneal catheter to a dialysis bag for a series of successive dialysis exchanges, comprising the steps of:
   (a) infusing of peritoneal dialysate from a regeneratable ambulatory dialysis bag having flexible sidewalls into the peritoneal cavity,
   (b) exchanging metabolities across the peritoneal membrane from the blood into said dialysate,
   (c) draining said dialysate from the peritoneal cavity into said dialysis bag, without mechanical pumping,
   (d) circulating make-up dialysis fluid through said hollow fibers located in said bag,
   (e) regenerating said dialysate in said bag by hollow fiber exchange of metabolites in said peritoneal dialysate with said make-up dialysis fluid in said fibers without removal of proteins from said peritoneal dialysate,
   (f) reinfusing the cleansed peritoneal dialysate from said bag into the peritoneal cavity for continued peritoneal dialysis, and
   (g) rolling up the emptied dialysis bag for carrying by the peritoneal dialysis patient until the next regeneration, while said bag remains attached to the peritoneal catheter of said patient.

6. The method of claim 5 wherein the peritoneal dialysate being regenerated in the dialysis bag is agitated during separate regeneration to shorten the time necessary for metabolite equilibration.

7. The method of claim 5 wherein the regeneration of the peritoneal dialysate further includes the step of ultrafiltering a determined amount of water from said bag to maintain a set volume of dialysate in said bag.

* * * * *